US011325984B2

(12) United States Patent
Kokaji (10) Patent No.: US 11,325,984 B2
(45) Date of Patent: *May 10, 2022

(54) METHOD FOR SEPARATING CELLS USING IMMUNOROSETTES AND MAGNETIC PARTICLES

(71) Applicant: StemCell Technologies Canada Inc., Vancouver (CA)

(72) Inventor: Andy Isamu Kokaji, Vancouver (CA)

(73) Assignee: StemCell Technologies Inc., Vancouver (CA)

(*) Notice: Subject to any disclaimer, the term of this patent is extended or adjusted under 35 U.S.C. 154(b) by 446 days.

This patent is subject to a terminal disclaimer.

(21) Appl. No.: 16/108,707

(22) Filed: Aug. 22, 2018

(65) Prior Publication Data

US 2019/0040357 A1 Feb. 7, 2019

Related U.S. Application Data

(63) Continuation of application No. 14/775,987, filed as application No. PCT/CA2014/000214 on Mar. 12, 2014, now Pat. No. 10,081,793.

(Continued)

(51) Int. Cl.
*G01N 33/569* (2006.01)
*C07K 16/42* (2006.01)
(Continued)

(52) U.S. Cl.
CPC .......... *C07K 16/4283* (2013.01); *C07K 16/28* (2013.01); *C07K 16/2896* (2013.01);
(Continued)

(58) Field of Classification Search
CPC .......... C12N 5/0634; G01N 33/56972; G01N 33/54326; G01N 33/56966; G01N 1/40
See application file for complete search history.

(56) References Cited

U.S. PATENT DOCUMENTS

2011/0286916 A1* 11/2011 Aste-Amezaga ....... A61P 35/00
424/1.49

FOREIGN PATENT DOCUMENTS

CA 2725132 A1 12/2000
WO WO 2012083020 A2 6/2012

OTHER PUBLICATIONS

Janeway et al. Immunobiology: the Immune System in Health and Disease (1999), Elsevier Science Ltd/Garland Publishing, New York, NY, Fourth Edition, pp. 86-88 (Year: 1999).*

(Continued)

*Primary Examiner* — Bao-Thuy L Nguyen
*Assistant Examiner* — Xiaoyan Zou
(74) *Attorney, Agent, or Firm* — Bereskin & Parr LLP/S.E.N.C.R.L; Micheline Gravelle (57) ABSTRACT

The present invention relates to methods for separating target cells from non-target cells using immunorosettes and magnetic particles. The method involves contacting a sample containing target cells and secondary targets such as erythrocytes with an antibody composition which allows immunorosettes of the target cells and the secondary targets to form. The sample is subsequently contacted with a second antibody composition which allows the binding of magnetic particles to the formed immunorosettes and free secondary targets. The immunorosettes and secondary targets labeled with magnetic particles are separated from non-target cells using a magnetic field. The antibody composition optionally contains bifunctional antibodies or tetrameric antibody complexes.

15 Claims, 6 Drawing Sheets

Related U.S. Application Data (60) Provisional application No. 61/929,674, filed on Jan. 21, 2014, provisional application No. 61/788,907, filed on Mar. 15, 2013.

(51) Int. Cl.
  *C07K 16/28* (2006.01)
  *G01N 1/40* (2006.01)

(52) U.S. Cl.
  CPC ......... *G01N 1/40* (2013.01); *G01N 33/56966* (2013.01); *G01N 33/56972* (2013.01); *C07K 2317/31* (2013.01)

(56) References Cited

OTHER PUBLICATIONS

Almagro et al. "Humanization of Antibodies", Frontiers in Bioscience 13, 1619-1633, 2008 (Year: 2008).*

Goel et al. "Plasticity within the Antigen Combining Site May Manifest as Molecular Mimicry in the Humoral Immune Response", The Journal of Immunology 173(12):7358-7367, 2004 (Year: 2004).*

Edwards et al. "The remarkable flexibility of the human antibody repertoire; isolation of over one thousand different antibodies to a single protein, BLyS" J. Mol. Biol. (2003) 334, 103-118, DOI: 10.1016/j.jmb.2003.09.054 (Year: 2003).*

Lloyd et al. "Modelling the human immune response: performance of a 10e11 human antibody repertoire against a broad panel of therapeutically relevant antigens", Protein Engineering, Design and Selection, vol. 22, Issue 3, Mar. 1, 2009, pp. 159-168 (Year: 2009).*

Brown et al. "Tolerance of single, but not multiple, amino acid replacements in antibody VH CDR 2: a means of minimizing B cell wastage from somatic hypermutation?", J Immunol. May 1996;156(9):3285-91 (Year: 1996).*

Vajdos et al. "Comprehensive functional maps of the antigen-binding site of an anti-ErbB2 antibody obtained with shotgun scanning mutagenesis" J Mol Biol. Jul. 5, 2002;320(2):415-28, DOI: 10.1016/S0022-2836(02)00264-4 (Year: 2002).*

Chang, C., Rossi, E.A., and Sharkey, R.M. (2011). The Dock-and-Lock (DNL) Approach to Novel Bispecific Antibodies. In R.E. Kontermann (Ed.), Bispecific Antibodies (1st Edition, p. 199-216), Heidelberg: Springer.

Ellerman, D. and Scheer, J.M. (2011). Generation of Bispecific Antibodies by Chemical Conjugation. In R.E. Kontermann (Ed.), Bispecific Antibodies (1st Edition, p. 47-63), Heidelberg: Springer.

Kim, J.H. and Hong, H.J. (2012) Humanization by CDR Grafting and Specificity-Determining Residue Grafting. In P. Chames (Ed.), Antibody Engineering: Methods and Protocols (2nd Edition, p. 237-245). New York: Humana Press.

Moldenhauer, G. (2011). Bispecific Antibody from Hybrid Hybridoma. In R.E. Kontermann (Ed.). Bispecific Antibodies (1st Edition, p. 29-46). Heidelberg:Springer Berlin.

Zuccolo, J., et al. "Efficient isolation of highly purified tonsil B lymphocytes using RosetteSep with allogeneic human red blood cells", BMC Immunology, Biomed Central, London GB, vol. 10, No. 1, May 27, 2009, p. 30.

* cited by examiner

Cell separation using a combination of non-magnetic and magnetic particles

Enrichment of CD3+ CD4+ T cells from erythrocyte depleted human PBMCs with pegylated polystyrene beads

Enrichment of CD3+ CD4+ T cells from human peripheral whole blood using immunomagnetic cell separation of immunorosettes.

Enrichment of lymphocyte populations from human peripheral whole blood using immunomagnetic cell separation of immunorosettes.

- CD3+ T cells
- CD3+CD4+ T cells
- CD3-CD19+ B cells
- CD3-CD56+ NK cells

Enrichment of human CD3+ CD4+ T cells using MACSxpress with or without additional erythrocyte depletion using immunomagnetic cell separation.

Enrichment of CD3+ T cells from human peripheral whole blood using immunorosettes and density separation, erythrocyte aggregation and immunomagnetic separation or immunorosettes and immunomagnetic separation.

☐ A: Ammonium chloride lysed whole blood
☐ B: Immunorosettes and density separation
▨ C: Erythrocyte aggregation and immunomagnetic separation
■ D: Immunorosettes and immunomagnetic separation

METHOD FOR SEPARATING CELLS USING IMMUNOROSETTES AND MAGNETIC PARTICLES

This application is a continuation application of U.S. patent application Ser. No. 14/775,987, filed on Sep. 14, 2015 (now patent Ser. No. 10/081,793), which is a national phase of International Application No. PCT/CA2014/000214, filed Mar. 12, 2014 (which designates the United States) which claims the benefit of U.S. Provisional Patent Application No. 61/788,907, filed on Mar. 15, 2013 (now abandoned) and U.S. Provisional Patent Application No. 61/929,674, filed Jan. 21, 2014 (now abandoned), which are incorporated herein in their entirety.

FIELD OF THE DISCLOSURE

The present disclosure relates to methods for separating cells using immunorosettes and magnetic particles.

BACKGROUND

In many applications it is desirable to enrich, or alternatively deplete, certain cell populations in a biological sample. The fields of hematology, immunology and oncology rely on samples of peripheral blood and cell suspensions from related tissues such as bone marrow, spleen, thymus and fetal liver. The separation of specific cell types from these heterogeneous samples is key to research in these fields. Purified populations of immune cells such as T cells and B cells are necessary for the study of immune function and are used in immunotherapy. Investigation of the cellular, molecular and biochemical processes require analysis of certain cell types in isolation. Numerous techniques have been used to isolate lymphocyte subsets such as T cells, B cells and natural killer (NK) cells and granulocytes such as neutrophils, basophils and eosinophils.

Hematopoietic cells and immune cells have been separated on the basis of physical characteristics such as density and through direct targeting with magnetic particles. The advent of monoclonal antibodies against cell surface antigens has greatly expanded the potential to distinguish and separate distinct cell types. There are two basic approaches to separating cell populations from blood and related cell suspensions using monoclonal antibodies. They differ in whether it is the desired or undesired cells which are distinguished/labelled with the antibody(s). In positive selection techniques, the desired cells are labelled with antibodies and removed from the remaining unlabelled/unwanted cells. In negative selection, the unwanted cells are labelled and removed. Antibody and complement treatment and the use of immunotoxins is a negative selection technique, whereas fluorescence assisted cell sorting (FACS) and most bulk immunoadsorption techniques can be adapted to both positive and negative selection. In immunoadsorption techniques, cells are selected with monoclonal antibodies and preferentially bound to a surface which can be removed from the remainder of the cells e.g. column of beads, flasks, magnetic particles. Immunoadsorption techniques have won favour clinically and in research because they maintain the high specificity of targeting cells with monoclonal antibodies, but unlike FACS, they can be scaled up to deal directly with the large numbers of cells in a clinical harvest and they avoid the dangers of using cytotoxic reagents such as immunotoxins and complement. They do however, require the use of a "device" or cell separation surface such as a column of beads, panning flask or magnet.

Density separations are commonly used to isolate peripheral blood mononuclear cells from granulocytes and erythrocytes. FICOLL™ (GE Healthcare Life Sciences, Chalfont, United Kingdom) is the most popular density solution used for this application. In a FICOLL™ density separation whole blood is layered over FICOLL™, and then centrifuged. The erythrocytes and granulocytes settle with the pellet and the mononuclear cells remain at the FICOLL: plasma interface. The success of this technique relies on the difference in density between mononuclear cells and granulocytes. If whole blood is stored for more than 24 hours the granulocytes change density and will not pellet with the erythrocytes. Suspensions of pure mononuclear cells cannot be obtained from stored blood or samples with altered cell density in a single density separation. RosetteSep is a commercially available immunodensity cell separation product from STEMCELL Technologies Inc. (Vancouver, Canada) that utilizes density gradient centrifugation to enrich cells from erythrocyte containing samples such as human peripheral whole blood by forming immunorosettes between undesired nucleated cells with erythrocytes. Although immunodensity cell separation can efficiently enrich nucleated cell populations from human peripheral whole blood, there can be residual erythrocyte contamination in the final enriched cell sample. For more information on the use of density gradient centrifugation for the separation of immunorosettes see U.S. Pat. No. 6,448,075 to Thomas, which is incorporated herein by reference.

Current cell separation methods using immunomagnetic negative selection methods for the isolation of immune cells, hematopoietic stem cells and circulating epithelial tumor cells typically involve an initial step to deplete erythrocytes followed by antibody mediated adherence to a device or artificial particle. Several commercial cell separation products are available that utilize a pre-processing step to reduce the erythrocyte content of peripheral whole blood such as hypotonic erythrocyte lysis, FICOLL™ density centrifugation or a gravity sedimentation approach prior immunomagnetic cell separation (Miltenyi Biotec Inc., Gladbach, Germany, Life Technologies Corp., Carlsbad, USA, STEMCELL Technologies Inc., Vancouver, Canada). Recently, a new method has been described (see PCT/EP2012/073083, which is incorporated herein by reference) that combines gravity sedimentation of erythrocytes with immunomagnetic cell separation in a single step to enrich for desired cells from peripheral human whole blood. This method however requires an additional immunomagnetic depletion step to further reduce erythrocyte contamination in the enriched sample.

In view of the foregoing, there is a need in the art to provide novel methods for improving erythrocyte removal and separating desired cells or removing unwanted cells from biological samples containing erythrocytes without the need for pre-processing or using time consuming gravity sedimentation approaches. There is currently no soley immunomagnetic cell separation method for the negative selection of cells directly from erythrocyte containing samples such as, but not limited to human peripheral whole blood without reducing the erythrocyte content by density centrifugation, agglutination or hypotonic lysis of whole blood either prior to or in combination with immunomagnetic cell separation.

SUMMARY

The present inventor has developed a method for separating target cells by immunorosetting the target cells with secondary targets such as erythrocytes already existing in, or added to the sample, and subsequently labeling the immunorosettes with particles that facilitate the removal of the immunorosette-particle complexes. In one embodiment, the particles are magnetic particles.

The methods of the disclosure can efficiently separate target cells from a complex sample while improving erythrocyte depletion compared to existing methods. With the current disclosure there is no need for pre-processing a sample with a significant erythrocyte content (>1 erythrocyte per nucleated cell) prior to subjecting the sample to the immunomagnetic cell separation procedure. A further benefit of the magnetic particle approach is that since it is an immunomagnetic cell separation approach, it can be fully automated thereby further reducing sample handling and minimizing exposure to blood borne pathogens such as viruses or parasites.

Accordingly, in one embodiment, the present disclosure provides a selection method for separating target cells from non-target cells in a sample comprising target cells, secondary targets and non-target cells, the method comprising:
  a. contacting the sample with a first antibody composition comprising (a) at least one antibody that binds to the target cells linked, either directly or indirectly, to (b) at least one antibody that binds to the secondary targets, under conditions to allow immunorosettes of the target cells and the secondary targets to form,
  b. contacting the sample with a second antibody composition comprising (a) at least one antibody that binds to the secondary targets either singly or within the immunorosettes, linked, either directly or indirectly, to (b) at least one antibody that binds to particles, under conditions to allow binding of the particles to the immunorosettes and/or the secondary targets, and
  c. separating the immunorosette-particle complexes and/or the secondary target-particle complexes from the sample to obtain a sample enriched for the target cells.

In one embodiment, the secondary targets are erythrocytes.

In another embodiment, the secondary targets are granulocytes.

In another embodiment, the secondary targets are beads, optionally polystyrene beads coated with a polymer such as polyethylene glycol (PEG).

In another embodiment, the secondary targets are added to the sample prior to separation.

In another embodiment, the particles are magnetic particles.

In another embodiment, the particles are non-magnetic particles.

In another embodiment, the secondary targets have a density similar to a cell and the particles have a density different from a cell.

In another embodiment, the selection method is a positive selection method to select for a desired cell and the target cell is the desired cell.

In another embodiment, the selection method is a negative selection method to remove a non-desired cell from the sample and the target cell is the non-desired cell.

In another embodiment, the immunorosette-magnetic particle complexes and/or the secondary target-magnetic particle complexes are separated from the sample in step c) by placing the sample in a magnetic field gradient of sufficient strength to separate the immunorosette-magnetic particle complexes and/or the secondary target-magnetic particle complexes from the sample.

In another embodiment, the immunorosette-magnetic particle complexes are separated from the sample in step c) by density separation.

In another embodiment, the immunorosette-magnetic particle complexes are separated from the sample in step c) by sedimentation.

In another embodiment, the method further comprises:
  d. separating the target cells from the immunorosette-magnetic particle complexes.

In another embodiment, the target cells are separated from the immunorosette-magnetic particle complexes by physical, chemical, enzymatic or thermal dissociation.

In another embodiment, the method further comprises:
  d. lysis of the erythrocytes in the immunorosettes and
  e. separation of the target cells from the lysed erythrocytes and the magnetic particles.

In another embodiment, the sample is whole blood, bone marrow, fetal liver, cord blood, a buffy coat suspension, a leukapheresis sample, a pleural and periotoneal effusion or a sample of thymocytes and splenocytes.

BRIEF DESCRIPTION OF THE DRAWINGS

The disclosure will now be described in relation to the drawings in which.

DETAILED DESCRIPTION

Methods of the Disclosure

The present disclosure relates to a method for separating target cells from non-target cells from a sample containing target cells, secondary targets and non-target cells by immunorosetting the target cells with the secondary targets and subsequently binding said immunorosettes and secondary targets to particles.

In one aspect, the present disclosure provides a selection method for separating target cells from non-target cells in a sample comprising target cells, secondary targets and non-target cells, the method comprising:
- a) contacting the sample with a first antibody composition comprising (a) at least one antibody that binds to the target cells linked, either directly or indirectly, to (b) at least one antibody that binds to the secondary targets, under conditions to allow immunorosettes of the target cells and the secondary targets to form,
- b) contacting the sample with a second antibody composition comprising (a) at least one antibody that binds to the secondary targets either singly or within the immunorosettes, linked, either directly or indirectly, to (b) at least one antibody that binds to particles, under conditions to allow binding of the particles to the immunorosettes and/or the secondary targets, and
- c) separating the immunorosette-particle complexes and/or the secondary target-particle complexes from the sample to obtain a sample enriched for the non-target cells.

The method can be used in both positive and negative selection protocols. In a positive selection protocol, desired cells are the target cells and are removed from a sample. In a negative selection protocol, desired cells are the non-target cells and remain in the sample following the selection protocol such that the remaining sample is enriched for the desired cells.

As used herein, the term "target cell" is a cell that is targeted by binding to the first antibody composition. The target cell is optionally a nucleated cell. In a positive selection protocol, the desired cell is the target cell. In a negative selection protocol, the desired cell is not the target cell. Rather, the desired cell is a non-target cell.

As used herein, the term "non-target cell" is a cell in the sample that does not bind to the first or second antibody composition. In a positive selection method, the non-target cell is not the desired cell. In a negative selection method the non-target cell is the desired cell.

As used herein, the term "secondary target" is a cell or other body such as a particle, bead or aggregate that binds to the first and second antibody composition and is to be removed from the sample. The secondary target is removed from the sample in both positive and negative selection protocols. In one embodiment, the secondary target is an erythrocyte. In another embodiment, the secondary target is a granulocyte. In another embodiment, the secondary target is a bead such as a polystyrene bead. The bead may be coated with a polymer such as PEG. In some embodiments, the secondary target is added to the sample prior to performing the selection method. For example, beads may be added to the sample.

In one embodiment, the particles are magnetic particles. In another embodiment, the particles are non-magnetic particles. One example of non-magnetic particles useful in the methods described herein are buoyant particles. Immunorosettes which include buoyant particles will float when placed in an appropriate buffer, thereby allowing separation of the immunorosettes from a sample.

In a negative selection protocol, the desired cells are not immunorosetted and remain in the sample following the removal of the immunorosettes labeled with the particles. Accordingly, the non-desired cells are the "target cells" to be removed from the sample along with the secondary targets and the desired cells are "non-target cells". In a negative selection, the antibody composition will contain at least one antibody specific for the cells that one wishes to remove from the sample. Accordingly, the present disclosure provides a negative selection method for enriching and recovering desired cells in a sample containing desired cells, secondary targets, and non-desired cells comprising:
- a) contacting the sample with a first antibody composition comprising (a) at least one antibody that binds to the non-desired cells linked, either directly or indirectly, to (b) at least one antibody that binds to the secondary targets, under conditions to allow immunorosettes of the non-desired cells and the secondary targets to form,
- b) contacting the sample with a second antibody composition comprising (a) at least one antibody that binds to the secondary targets either singly or within the immunorosettes, linked, either directly or indirectly, to (b) at least one antibody that binds to particles, under conditions to allow binding of the particles to the immunorosettes and/or the secondary targets, and
- c) separating the immunorosette-particle complexes and/or the secondary target-particle complexes from the sample to obtain a sample enriched in the desired cells.

In a positive selection protocol, the desired cells are the target cells. The desired cells are immunorosetted to the secondary targets and subsequently bound to the particles. In such an embodiment, the method can further include the step of separating the desired cells from the immunorosettes. In a positive selection, the antibody composition will contain at least one antibody specific for the desired cells that one wishes to remove from the sample. Accordingly, the present disclosure provides a positive selection method for recovering desired cells from a sample containing the desired cells, secondary targets, and non-desired cells comprising:
- a) contacting the sample with a first antibody composition comprising (a) at least one antibody that binds to the desired cells linked, either directly or indirectly, to (b) at least one antibody that binds to the secondary targets, under conditions to allow immunorosettes of the desired cells and the secondary targets to form,
- b) contacting the sample with a second antibody composition comprising (a) at least one antibody that binds to the secondary targets either singly or within the immunorosettes, linked, either directly or indirectly, to (b) at least one antibody that binds to particles, under conditions to allow binding of the particles to the immunorosettes and/or the secondary targets, and
- c) separating the immunorosette-particle complexes and/or the secondary target-particle complexes from the sample to obtain a sample enriched in the desired cells within the immunorosette-particle complexes.

In one embodiment, the positive selection method includes the disaggregation of the immunorosette-particle complex to separate the desired cells from the immunorosette-particle complex through but not limited to, physical, chemical, enzymatic, or thermal dissociation. In one embodiment, if the secondary targets are erythrocytes, a further step includes the hypotonic lysis of the erythrocytes in the immunorosettes and separation of the desired cells from the lysed erythrocytes and the magnetic particles. The resulting positively selected desired cells will be free of bound magnetic particles.

The immunorosettes bound to particles formed in step (b) above for either negative or positive selection can be separated from the non-magnetic non-target cells using a variety of techniques.

In the preferred embodiment, the particles are magnetic particles and the sample, containing the immunorosettes labeled with magnetic particles, is placed into a magnetic field. The immunorosettes labeled with magnetic particles migrate towards the magnetic field and are held in place allowing the non-magnetic non-target cells to be easily separated from the immunorosettes labeled with magnetic particles.

In another embodiment, the sample containing the immunorosettes labeled with particles is layered over a buoyant density solution (such as FICOLL™) and centrifuged. The immunorosettes labeled with the particles pellet due to their increased density and the target cells remain at the interface between the buoyant density solution and the sample. The target cells are then removed from the interface for further use.

In another embodiment, the sample containing the immunorosettes obtained in step (a) or immunorosette-particles complexes obtained in step (b) is mixed with a sedimentation reagent (such as hydroxyethyl starch, gelatin or methyl cellulose) and the immunorosettes or immunorosette-particle complexes are permitted to sediment. The desired cells remain in suspension and are removed for further use.

The methods of the disclosure may be used in the processing of biological samples that contain erythrocytes including blood (in particular, cord blood and whole blood) bone marrow, fetal liver, buffy coat suspensions, leukapheresis samples, pleural and peritoneal effusions and suspensions of thymocytes and splenocytes. The method can be used to separate desired cells or removing unwanted cells from biological samples containing erythrocytes such as whole blood or whole bone marrow without the need for pre-processing or using time consuming gravity sedimentation approaches prior to, or in combination with, immunomagnetic cell separation approaches. This offers a significant advantage of the method of the disclosure over the prior art methods. In particular, the present disclosure can reduce the final erythrocyte content to less than 5% of the final enriched population which is an improvement on existing methods. Furthermore, the entire procedure can be performed using only immunomagnetic cell separation without the aid of non-magnetic erythrocyte depletion methods such as density gradient centrifugation, density sedimentation or hypotonic lysis. Although the preferred embodiment uses only a magnetic field to separate the magnetically labeled immunorosettes, the current procedure still retains its utility for use with density gradient centrifugation methodology or sedimentation reagents.

The method of the disclosure can be used to prepare enriched samples of any cell type including, but not limited to, T cells, B cells, NK cells, dendritic cells, monocytes, basophils, mast cells, progenitor cells, stem cells and tumor cells.

In one embodiment, the method of the disclosure may be used to prepare a cell preparation from samples such as blood and bone marrow, which is enriched in a selected differentiated cell type such as T cells, B cells, NK cells, monocytes, dendritic cells, basophils and plasma cells. This will enable studies of specific cell to cell interactions including growth factor production and responses to growth factors. It will also allow molecular and biochemical analysis of specific cells types. Cell preparations enriched in NK cells, dendritic cells and T cells may also be used in immune therapy against certain malignancies.

Antibody and Particle Compositions

The disclosure includes the antibody and particle compositions for use in the methods described herein. The first antibody composition will contain (a) at least one antibody that binds to an antigen on the target cell, linked either directly or indirectly, to (b) at least one antibody that binds to the secondary target.

In one embodiment, the second antibody composition will contain (c) at least one antibody that binds to the secondary target linked, either directly or indirectly, to (d) at least one antibody that binds to a particle.

In a preferred embodiment, the second antibody composition will be directly bound to a particle using conventional techniques that are readily apparent to those skilled in the art such as physical adsorption or chemical conjugation. In one aspect, the second antibody composition bound to a particle will contain (c) at least one antibody that binds to the secondary target linked, either directly or indirectly, to (d) at least one antibody that binds to the same secondary target. In another aspect, the second antibody composition will contain (c) at least one antibody that binds to the secondary target which is directly bound to the particle using conventional techniques that are readily apparent to those skilled in the art such as physical adsorption or chemical conjugation.

The term "at least one antibody" means that the antibody composition includes at least one type of antibody (as opposed to at least one antibody molecule). One type of antibody means an antibody that binds to a particular antigen. For example, antibodies that bind to the antigen CD3 are considered one type of antibody. Preferably, the antibody compositions of the disclosure contain (a) more than one antibody type that binds to target cells.

In one aspect, the first antibody composition of the present disclosure comprises (a) at least one antibody specific for a target cell and (b) at least one antibody specific for the secondary target. By "indirectly linked" it is meant that antibody (a) and antibody (b) are not directly covalently linked to each other but are attached through a linking moiety such as an immunological complex. In a preferred embodiment, the first antibody composition contains at least one antibody to the target cell (a) that is indirectly linked to at least one antibody specific for the secondary target (b) by preparing a bi-specific tetrameric antibody complex. A bi-specific tetrameric antibody complex may be prepared by mixing (a) the first monoclonal antibody which is capable of binding to the target cells, and (b) second monoclonal antibody capable of binding the secondary target cells. The first and second monoclonal antibody are from a first animal species. The first and second antibodies are reacted with approximately an equimolar amount of monoclonal antibodies of a second animal species which are directed against the Fc-fragments of the antibodies of the first animal species. The first and second antibodies may also be reacted with an about equimolar amount of the full length or F(ab')2 fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing the same).

The second antibody composition of the present disclosure comprises (c) at least one antibody specific for the secondary target cell and (d) at least one antibody specific for the particle. By "indirectly linked" it is meant that antibody (c) and antibody (d) are not directly covalently linked to each other but are attached through a linking moiety such as an immunological complex. The second antibody composition contains at least one antibody to the secondary target cell (c) that is indirectly linked to at least one antibody specific for the particle (d) by preparing a bi-specific tetrameric antibody complex as described for the first antibody composition.

In another embodiment, the second antibody composition of the present disclosure comprises (c) at least one antibody specific for the secondary target cell and (d) at least one antibody specific for same secondary target indirectly linked by preparing a mono-specific tetrameric antibody complex. A mono-specific tetrameric antibody complex may be prepared by mixing the monoclonal antibody which is capable of binding to the secondary target cells from a first animal species with an equimolar amount of monoclonal antibodies of a second animal species which are directed against the Fc-fragments of the antibodies of the first animal species. The antibodies from the first animal species may also be reacted with an about equimolar amount of the full length or F(ab')2 fragments of monoclonal antibodies of a second animal species which are directed against the Fc-fragments of the antibodies of the first animal species.

In a preferred embodiment, the second antibody composition containing mono-specific tetrameric antibody complexes specific for the secondary targets are directly bound to the particle using conventional techniques that are readily apparent to those skilled in the art such as physical adsorption or chemical conjugation.

In another embodiment, the antibody specific for the target cells is linked directly to the antibody specific for the secondary target and the antibody specific for the secondary target is linked directly to the antibody specific for the magnetic particle. In one embodiment, the antibody composition of the present disclosure contains bifunctional antibodies comprising (a) at least one antibody specific for the target cells linked directly to (b) at least one antibody specific for the secondary targets and a second bifunctional antibody comprising (c) at least one antibody specific for the secondary targets linked directly to (d) at least one antibody specific for the particles. Bifunctional antibodies may be prepared by chemically coupling one antibody to the other using conventional techniques that are readily apparent to those of skill in the art as those disclosed in Ellerman and Scheer [1].

In another embodiment, the antibody composition contains bispecific antibodies. The first bispecific antibodies contains a variable region of an antibody specific for the secondary targets and a variable region specific for at least one antigen on the surface of the target cells to be separated. The second bispecific antibody contains a variable region of an antibody specific for the secondary targets and the particles. The bispecific antibodies may be prepared by forming hybrid hybridomas. The hybrid hybridomas may be prepared using the procedures known in the art such as those disclosed in Moldenhauer [2]. Bispecific antibodies may also be constructed by expression of recombinant immunoglobulin gene constructs as described by Chang, Rossi, and Sharkey [3].

In one embodiment, the secondary targets are erythrocytes and the antibody specific for the erythrocytes is anti-glycophorin A. The anti-glycophorin A antibodies contained in the antibody composition of the disclosure are used to bind the erythrocytes. Examples of monoclonal antibodies specific for glycophorin A are 10F7MN (U.S. Pat. No. 4,752,582, Cell lines: ATCC accession numbers HB-8162), and D2.10 (Immunotech, Marseille, France). Preferably, the antibody specific for the target cells is a combination of antibodies. The combination of antibodies may be specific for a number of cell types so that many target cell types may be removed from the sample. When using a combination of antibodies, each antibody will be linked (either directly or indirectly) to an antibody specific for erythrocytes.

In a one embodiment, the particles are magnetic particles and the mono-specific tetrameric antibody complex specific for the secondary targets are directly bound to the magnetic particle using conventional techniques such as physical adsorption or chemical conjugation that are readily apparent to those of skill in the art.

In another embodiment, the particles are magnetic particles and the antibody specific for the secondary targets are directly bound to the magnetic particle using conventional techniques such as physical adsorption or chemical conjugation that are readily apparent to those of skill in the art.

In another embodiment, the particles are magnetic particles and the antibody specific for the magnetic particle is anti-dextran. The anti-dextran antibodies contained in the antibody composition of the disclosure are used to bind the magnetic particles which have been coated with a dextran polymer.

In another embodiment, the first antibody composition is a tetrameric complex comprising (a) anti-glycophorin A antibodies to bind the erythrocytes, (b) an antibody that binds to a target cell type that one wishes to immunorosette and (c) antibodies that bind the Fc portion of both (a) and (b), optionally F(ab')2 antibody fragments. The molar ratio of (a):(b):(c) may be approximately 1:3:4. When several types of cells are to be separated, complexes are made with several anti-target cell antibodies (b). The complexes may then be mixed together to form an antibody composition for use in the method of the disclosure. The second antibody composition is a mono-specific tetrameric complex comprising (a) anti-glycophorin A antibodies to bind the erythrocytes in immunorosettes, and (c) antibodies that bind the Fc portion of (a), optionally F(ab')2 antibody fragments. The molar ratio of (a):(c) may be approximately 1:1. The mono-specific tetrameric complexes specific for the secondary targets are directly bound to the magnetic particle using conventional techniques.

In another embodiment, the first antibody composition is a tetrameric complex comprising (a) anti-glycophorin A antibodies to bind the erythrocytes, (b) an antibody that binds to a target cell type that one wishes to immunorosette and (c) antibodies that bind the Fc portion of both (a) and (b), optionally F(ab')2 antibody fragments. The molar ratio of (a):(b):(c) may be approximately 1:3:4. When several types of cells are to be separated, complexes are made with several anti-target cell antibodies (b). The complexes may then be mixed together to form an antibody composition for use in the method of the disclosure. The second antibody composition is anti-glycophorin A antibodies directly bound to magnetic particles that can to bind individual erythrocytes and erythrocytes within immunorosettes.

In another embodiment, the first antibody composition is a tetrameric complex comprising (a) anti-glycophorin A antibodies to bind the erythrocytes, (b) an antibody that binds to a target cell type that one wishes to immunorosette and (c) antibodies that bind the Fc portion of both (a) and (b), optionally F(ab')2 antibody fragments. The molar ratio of (a):(b):(c) may be approximately 1:3:4. When several types of cells are to be separated, complexes are made with several anti-target cell antibodies (b). The complexes may then be mixed together to form an antibody composition for use in the method of the disclosure. The second antibody composition is a tetrameric complex comprising (a) anti-glycophorin A antibodies to bind the erythrocytes in immunorosettes, (d) an anti-dextran antibody that binds to a magnetic particle and (c) antibodies that bind the Fc portion of both (a) and (d), optionally F(ab')2 antibody fragments. The molar ratio of (a):(d):(c) may be approximately 1:3:4.

In one embodiment, the second antibody composition is a tetrameric antibody complex comprising (a) anti-glycophorin A antibodies to bind the erythrocytes in immunorosettes, (b) an anti-dextran antibody that binds to a magnetic particle and (c) antibodies that bind the Fc portion of both (a) and (d), optionally F(ab')2 antibody fragments. The molar ratio of (a):(d):(c) may be approximately 1:3:4. The second antibody composition is pre-loaded onto the magnetic particle prior to adding to the sample.

Within the context of the present disclosure, antibodies are understood to include monoclonal antibodies and polyclonal antibodies, antibody fragments (e.g., Fab, and F(ab') 2), chimeric antibodies, bifunctional or bispecific antibodies and tetrameric antibody complexes. Antibodies are understood to be reactive against a selected antigen on the surface of a target cell or erythrocyte if they bind with an appropriate affinity (association constant), e.g. greater than or equal to $10^7 M^{-1}$.

Monoclonal antibodies are preferably used in the antibody compositions of the disclosure. Monoclonal antibodies specific for selected antigens on the surface of nucleated cells may be readily generated using conventional techniques that are readily apparent to those of skill in the art.

The disclosure also contemplates aptamers or chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes selected antigens on the surface of differentiated cells or tumor cells. See for example, Kim and Hong [4].

The following non-limiting examples are illustrative of the present disclosure:

EXAMPLES

Example 1

Preparation of Tetrameric Antibody Complexes

In order to prepare a tetrameric antibody complex for use in the method of the present disclosure, the following protocol may be used: (a) take 1 mg of antibody specific for cells to be rosetted (e.g. anti-CD8, CD16, CD19, CD36, CD56, CD66b, etc.); (b) add 3 mg anti-glycophorin A antibody (against erythrocytes); mix well (c) then add 4.0 mg of P9 antibody or 2.72 mg of the P9 F(ab')2 antibody fragment. Incubate overnight at 37° C. The P9 antibody binds the Fc portion of the antibodies added in steps (a) and (b) resulting in a tetrameric antibody complex. For the second antibody composition, the following protocol may be used: (a) take 1 mg of antibody specific to erythrocytes (anti-glycophorin A); (b) add 1 mg of P9 antibody or 0.68 mg of P9 F(ab')2 antibody fragment. Alternatively, (a) take 1 mg of antibody specific to erythrocytes (anti-glycophorin A); (b) add 3 mg of anti-dextran antibody; mix well (c) then add 4.0 mg of P9 antibody or 2.72 mg of P9 F(ab')2 antibody fragment. Incubate overnight at 37° C. For more information on the preparation of tetramers see U.S. Pat. No. 4,868,109 to Lansdorp, which is incorporated herein by reference. Tetrameric antibody complexes incorporating different antibodies to antigens expressed or nucleated cells are prepared separately and then mixed.

The antibody compositions are made by combining various tetrameric antibody complexes depending on which cells one wishes to deplete. The concentration of the various tetrameric antibody complexes varies: typically antibodies to antigens expressed on nucleated cells are at 10-40 ug/mL in tetrameric complexes. The composition is then diluted 1/20 into the cells so the final concentrations of each anti-nucleated cell antibody in the cell suspensions is 0.5-2.0 ug/mL.

In one embodiment, the second antibody composition comprised of anti-glycophorin A antibodies in a monospecific tetrameric antibody complex is at a concentration of 20-400 ug/mL. The second composition is directly bound to a particle using conventional techniques such as physical adsorption or chemical conjugation that are readily apparent to those of skill in the art. The second antibody composition directly bound to the particle is then diluted 1/20 into the sample so the final concentration of anti-glycophorin A in the sample is 1-20 ug/m L.

In another embodiment, the second antibody comprised of anti-glycophorin A antibodies is at a concentration of 20-400 ug/mL. The second antibody is directly bound to a particle using conventional techniques such as physical adsorption or chemical conjugation that are readily apparent to those of skill in the art. The second antibody composition directly bound to the particle is then diluted 1/20 into the sample so the final concentration of anti-glycophorin A in the sample is 1-20 ug/mL.

In another embodiment, the second antibody composition comprised of anti-glycophorin A and anti-dextran antibodies is at a concentration of 20-400 ug/mL. The second composition is then diluted 1/20 into the immunorosetted cells so the final concentration of anti-glycophorin A in the cell suspension is 1-20 ug/mL.

Example 2

Preparation of Particles with Bound Tetrameric Antibody Complexes or Antibodies Against the Secondary Target.

In order to prepare a particle with bound tetrameric antibody complexes for use in the method of the present disclosure, the following protocol may be used: (a) take 200 ug of anti-glycophorin A antibody bound in a tetrameric antibody complex with 200 ug of P9 antibody; (b) add 80 mg of carboxydextran magnetic particles; and (c) incubate overnight at 15-37° C. The composition is then diluted 1/20 into the sample so the final concentration of anti-glycophorin A antibody is between 1-10 ug/mL.

In another embodiment, physical adsorption or chemical crosslinking of anti-glycophorin A to magnetic particles is performed using conventional techniques that are readily apparent to those of skill in the art. A non-limiting example illustrative of the present disclosure would be the EDC-NHS crosslinking of anti-glycophorin A antibody to a carboxydextran magnetic particle. The composition is then diluted 1/20 into the sample so the final concentration of anti-glycophorin A antibody is 1-10 ug/mL.

In another embodiment, (a) take 100 ug of anti-glycophorin A antibody bound in a tetrameric antibody complex with 600 ug of anti-dextran antibody and 600 ug of P9 antibody or 408 ug of P9 (F(ab')2 antibody fragment; then add (b) 13.3 mg of dextran-coated magnetic particles; and (c) incubate 5 minutes at room temperature. The composition is then diluted 1/20 into the cells so the final concentration of glycophorin A antibody is 1-10 ug/mL.

Example 3

Method of Immunomagnetic Cell Separation of Immunorosettes from Human Peripheral Whole Blood Using Mono-Specific Tetrameric Antibody Complexes Specific for the Secondary Targets Directly Bound to Magnetic Particles A negative selection protocol for immunorosetting cells from human peripheral whole blood using magnetic cell separation is set out below.
 1. Add 50 uL of the first antibody composition per mL of human peripheral whole blood.
 2. Add 50 uL of the second antibody composition directly bound to magnetic particles per mL of human peripheral whole blood.
 3. Incubate 5 minutes at room temperature.
 4. Dilute sample with an equal volume of phosphate buffered saline (PBS) and mix gently.
 5. Place the tube containing the sample into a magnet.
 6. Incubate 5 minutes at room temperature.
 7. Remove the enriched cells from the sample while the sample tube is retained within the magnet.
 8. Add an equivalent volume of the second antibody composition directly bound to magnetic particles as in step 2 to the diluted enriched sample
 9. Incubate 5 minutes at room temperature.
 10. Place the tube containing the sample into a magnet.
 11. Incubate 5 minutes at room temperature.
 12. Remove the enriched cells from the sample while the sample tube is retained within the magnet.

Figure 4:
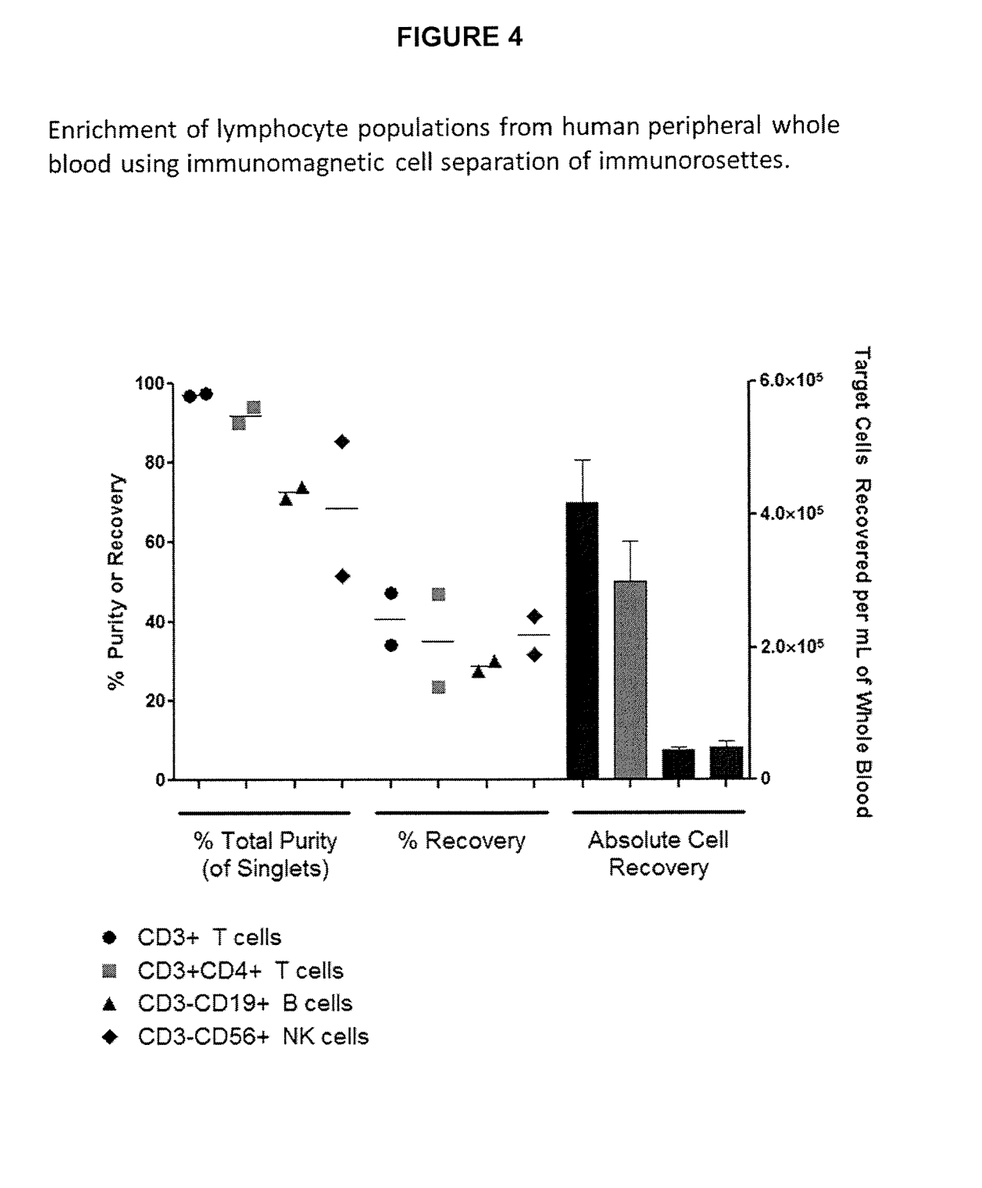
FIG. 4 shows enrichment of human CD3+ T cells, CD3+ CD4+ T cells, CD3− CD19+ B cells and CD3− CD56+ NK cells from human peripheral whole blood using immunomagnetic cell separation of immunorosettes according to example 3. Following immunomagnetic cell separation according to example 3, mean purities for each cell type indicated above was 97.2%, 92.0%, 73.9%, and 68.5%, with recovery values of 40.7%, 35.2%, 29.9%, and 36.6%, respectively.

A first antibody composition for the enrichment of a) CD3+ T cells, b) CD3+ CD4+ T cells, c) CD3− CD19+ B cells, and d) CD3− CD56+ NK cells from human peripheral whole blood each consisting of a cocktail of tetrameric antibody complexes containing antibodies against target cells and glycophorin A (secondary targets) was prepared. A second antibody composition consisting of a mono-specific tetrameric antibody complex containing antibodies against glycophorin A bound to carboxydextran magnetic particles was prepared. Following the method of the disclosure, mean purities for each cell type indicated above was a) 97.2%, b) 92.0%, c) 73.9% and d) 68.5%, with recovery values of a) 40.7%, b) 35.2%, c) 29.9%, and d) 36.6%, respectively as shown in FIG. 4.

Example 4

Method of Immunomagnetic Cell Separation of Immunorosettes from Human Peripheral Whole Blood Using Tetrameric Antibody Complexes Specific for the Secondary Targets and Magnetic Particles Preloaded onto Magnetic Particles A negative selection protocol for immunorosetting cells from human peripheral whole blood using magnetic cell separation is set out below.
 1. Add 50 uL of the first antibody composition per mL of human peripheral whole blood.
 2. Add 50 uL of the second antibody composition preloaded onto magnetic particles per mL of human peripheral whole blood.
 3. Incubate 5 minutes at room temperature.
 4. Dilute sample with an equal volume of phosphate buffered saline (PBS) and mix gently.
 5. Place the tube containing the sample into a magnet.
 6. Incubate 5 minutes at room temperature.
 7. Remove the enriched cells from the sample while the sample tube is retained within the magnet.
 8. Add an equivalent volume of the second antibody composition pre-loaded onto magnetic particles as in step 2 to the diluted enriched sample
 9. Incubate 5 minutes at room temperature.
 10. Place the tube containing the sample into a magnet.
 11. Incubate 5 minutes at room temperature.
 12. Remove the enriched cells from the sample while the sample tube is retained within the magnet.

Figure 3A:
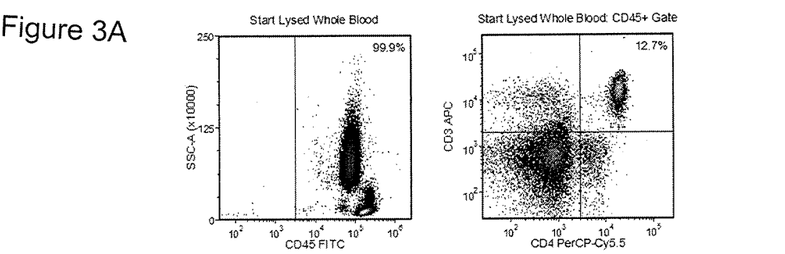
FIGS. 3A-3C shows enrichment of human CD3+ CD4+ T cells from human peripheral whole blood using immunomagnetic cell separation of immunorosettes according to example 4 and 5. Samples were stained with anti-human CD45 FITC, CD4 PerCP-Cy5.5 and CD3 APC and analyzed by flow cytometry. A) Following hypotonic lysis of erythrocytes in human peripheral blood, 99.9% of cells are CD45+ of which 12.7% are CD3+ CD4+ T cells. B) Following immunomagnetic cell separation according to example 4, 96.0% of cells are CD45+ of which are 94.6% CD3+ CD4+ T cells. C) Following immunomagnetic cell separation according to example 5, 99.8% of cells are CD45+ of which are 94.6% CD3+ CD4+ T cells.
Figure 3B:
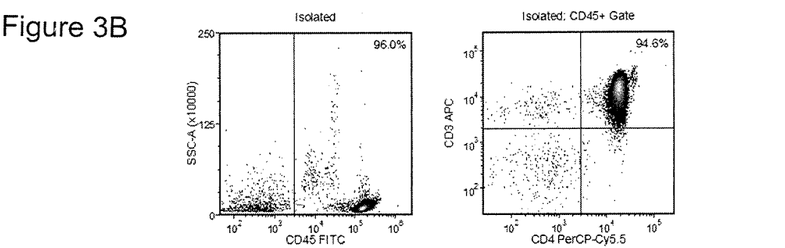

A first antibody composition for the enrichment of CD4+ T cells from human peripheral whole blood consisting of a cocktail of tetrameric antibody complexes containing antibodies against CD8, CD16, CD19, CD36, CD56, CD66b, TCRγδ and glycophorin A was prepared. A second antibody composition consisting of a tetrameric antibody complex containing antibodies against glycophorin A and dextran was prepared and preloaded onto carboxydextran magnetic particles. Following the method of the disclosure, 96.0% of cells were CD45+ of which, 94.6% were CD3+ CD4+ T cells as shown in FIG. 3B.

Example 5

Method of Immunomagnetic Cell Separation of Immunorosettes from Human Peripheral Whole Blood Using Antibodies Specific for the Secondary Targets Chemically Conjugated to Magnetic Particles A negative selection protocol for immunorosetting cells from human peripheral whole blood using magnetic cell separation is set out below.
 1. Add 50 uL of the first antibody composition per mL of human peripheral whole blood.
 2. Add 50 uL of the second antibody composition chemically conjugated to magnetic particles per mL of human peripheral whole blood.
 3. Add 50 uL of dextran coated magnetic particles per mL of human peripheral blood.
 4. Incubate 10 minutes at room temperature.
 5. Dilute sample with an equal volume of phosphate buffered saline (PBS) and mix gently.
 6. Place the tube containing the sample into a magnet.
 7. Incubate 5 minutes at room temperature.
 8. Remove the enriched cells from the sample while the sample tube is retained within the magnet.
 9. Add an equivalent volume of the dextran coated magnetic particles as in step 3 to the diluted enriched sample
 10. Incubate 5 minutes at room temperature.
 11. Place the tube containing the sample into a magnet.
 12. Incubate 5 minutes at room temperature.
 13. Remove the enriched cells from the sample while the sample tube is retained within the magnet.

Figure 3C:
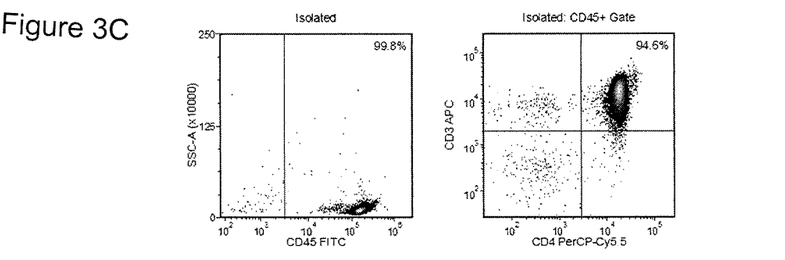

A first antibody composition for the enrichment of CD4+ T cells from human peripheral whole blood consisting of a cocktail of tetrameric antibody complexes containing antibodies against CD8, CD16, CD19, CD36, CD56, CD66b, TCRγδ and glycophorin A was prepared. A second antibody composition consisting of antibodies against glycophorin A chemically conjugated to carboxydextran magnetic particles was prepared. Following the method of the disclosure, 99.8% of cells were CD45+ of which, 94.6% were CD3+ CD4+ T cells as shown in FIG. 3C.

Example 6

Method of Immunomagnetic Cell Separation of Immunorosettes from Human Peripheral Whole Blood Using Carboxydextran Coated Magnetic Particles.

A negative selection protocol for immunorosetting cells from human peripheral whole blood using magnetic cell separation is set out below.
1. Add 50 uL of the first antibody composition per mL of human peripheral whole blood.
2. Add 50 uL of the second antibody composition per mL of human peripheral whole blood.
3. Incubate 10 minutes at room temperature.
4. Add 50 uL of carboxydextran coated magnetic particles per mL of human peripheral whole blood.
5. Incubate 5 minutes at room temperature.
6. Dilute sample with an equal volume of phosphate buffered saline (PBS) and mix gently.
7. Place the tube containing the sample into a magnet.
8. Incubate 5 minutes at room temperature.
9. Remove the enriched cells from the sample while the sample tube is retained within the magnet.
10. Add 5 uL of carboxydextran coated magnetic particles per mL of diluted enriched sample.
11. Incubate 5 minutes at room temperature.
12. Place the tube containing the sample into a magnet.
13. Incubate 5 minutes at room temperature.
14. Remove the enriched cells from the sample while the sample tube is retained within the magnet.

A first antibody composition for the enrichment of CD4+ T cells from human peripheral whole blood consisting of a cocktail of tetrameric antibody complexes containing antibodies against CD8, CD16, CD19, CD36, CD56, CD66b, TCRγδ and glycophorin A was prepared. A second antibody composition consisting of a tetrameric antibody complex containing antibodies against glycophorin A and dextran was prepared. Following the method of the disclosure, 92.6% purity of CD4+ T cells with a recovery of 24.7% was achieved as shown in Table 1.

Example 7

Method of Immunomagnetic Cell Separation of Immunorosettes from Human Peripheral Blood Mononuclear Cells (PBMC)

A negative selection protocol for immunorosetting cells from erythrocyte depleted human PBMCs using magnetic cell separation is set out below.
1. Add an equivalent or greater number of non-magnetic particles to the erythrocyte depleted human PBMC sample.
2. Add 50 uL of the first antibody composition per mL of sample.
3. Add 50 uL of the second antibody composition per mL of sample.
4. Incubate 10 minutes at room temperature.
5. Add 50 uL of magnetic particles per mL of sample.
6. Incubate 5 minutes at room temperature.
7. Dilute sample with an equal volume of PBS+2% FBS and mix gently.
8. Place the tube containing the sample into a magnet.
9. Incubate 5 minutes at room temperature.
10. Remove the enriched cells from the sample while the sample tube is retained within the magnet.
11. Add 5 uL of magnetic particles per mL of diluted enriched sample.
12. Incubate 5 minutes at room temperature.
13. Place the tube containing the sample into a magnet.
14. Incubate 5 minutes at room temperature.
15. Remove the enriched cells from the sample while the sample tube is retained within the magnet.

A first antibody composition for the enrichment of CD4+ T cells from human peripheral blood mononuclear cells consisting of a cocktail of tetrameric antibody complexes containing antibodies against CD8, CD16, CD19, CD36, CD56, CD66b, TCRγδ and anti-PEG was prepared. A second antibody composition consisting of a tetrameric antibody complex containing antibodies against PEG and dextran was prepared. Following the method of the disclosure, 96.6% of cells were CD45+ of which, 96.3% were CD3+ CD4+ T cells as shown in FIG. 2C.

Example 8

Enrichment of Human CD4+ T Cells from Peripheral Whole Blood Using Density Gradient Centrifugation or Immunomagnetic Separation of Immunorosettes.

This example demonstrates the enrichment of CD4+ T cells from whole peripheral blood using the method described in Example 6 compared to CD4+ T cells enriched using immunorosettes isolated using density gradient centrifugation (Table 1). A CD4+ T cell enrichment cocktail of tetrameric antibody complexes containing antibodies against CD8, CD16, CD19, CD36, CD56, CD66b, TCRγδ and glycophorin A was prepared. A second tetrameric antibody complex containing antibodies against glycophorin A and dextran was prepared. The results, shown in Table 1, demonstrate that the method of the disclosure results in 92.6% purity of CD4+ T cells with a recovery of 24.7%. In comparison, density gradient centrifugation of immunorosettes results in 80.6% purity of CD4+ T cells with 23.2% recovery primarily due to the presence of residual erythrocytes in the final enriched fraction (84.5% versus 97.5% CD45+ purity).

TABLE 1

Enrichment of Human CD3+ CD4+ T cells from peripheral whole blood using density gradient centrifugation or immunomagnetic separation of immunorosettes

| Immunorosette depletion method of CD4+ T cell enrichment (n = 4) | % CD45+ | % CD3+ CD4+ (of CD45+) | % CD45+ CD3+ CD4+ recovery | % CD45+ CD3+ CD4+ (of total) |
|---|---|---|---|---|
| Density gradient centrifugation | 84.5 +/− 7.8 | 96.6 +/− 0.5 | 23.2 +/− 5.5 | 80.6 +/− 7.9 |
| Immunomagnetic separation | 97.5 +/− 1.8 | 96.2 +/− 1.9 | 24.7 +/− 4.4 | 92.6 +/− 2.6 |

Example 9

Enrichment of Human CD4+ T Cells from Human PBMCs with PEGylated Polystyrene Beads.

Figure 1A:
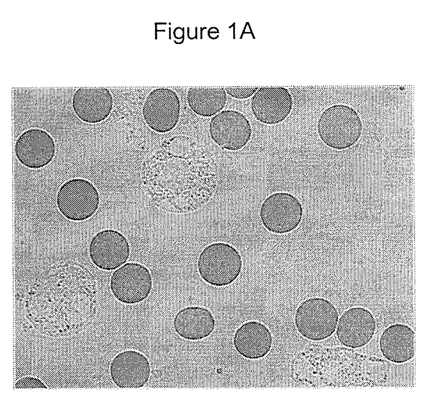
FIGS. 1A-1D shows a bright field image of A) peripheral human whole blood, B) peripheral human whole blood with immunorosettes, C) immunorosettes bound by magnetic particles and D) a magnified image of immunorosettes bound by magnetic particles as indicated by the arrow.
Figure 1B:
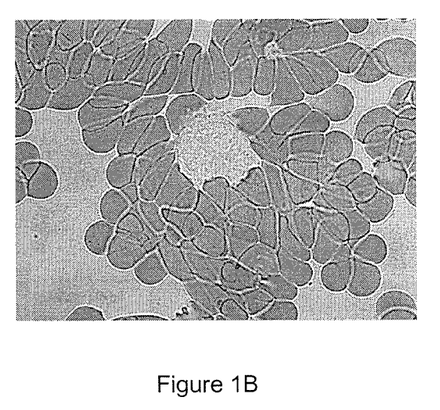
Figure 1C:
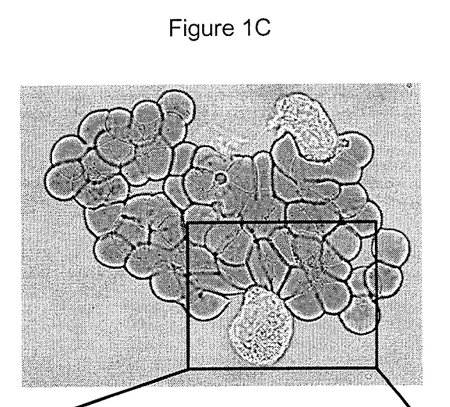
Figure 1D:
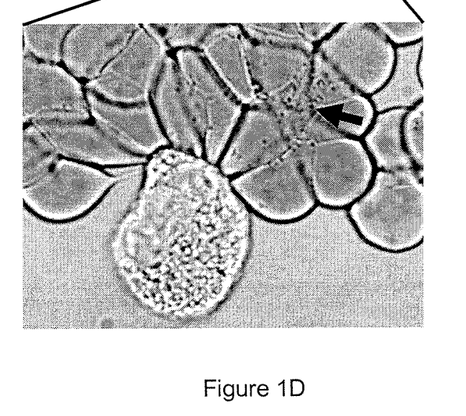
Figure 2A:
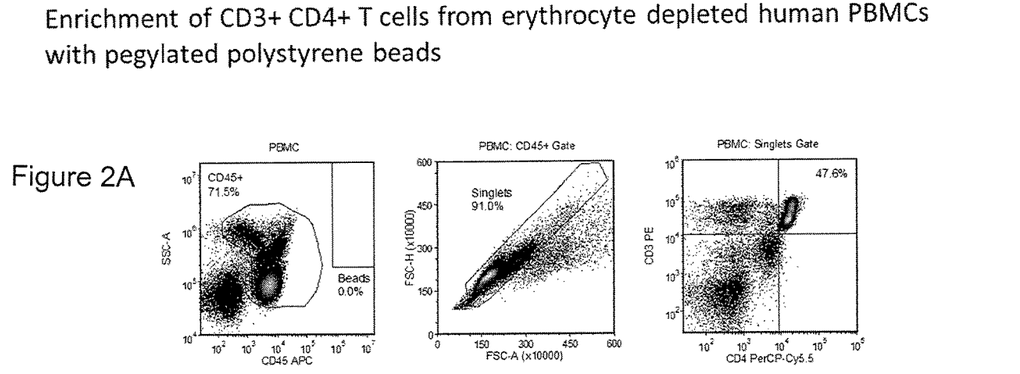
FIGS. 2A-2C shows enrichment of human CD3+ CD4+ T cells from erythrocyte depleted human peripheral blood mononuclear cells with pegylated polystyrene beads.
Figure 2B:
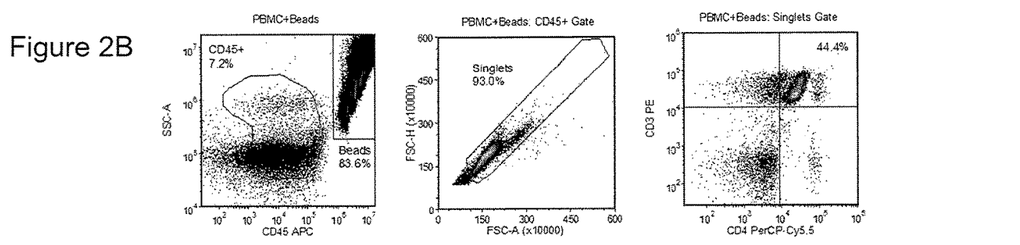
Figure 2C:
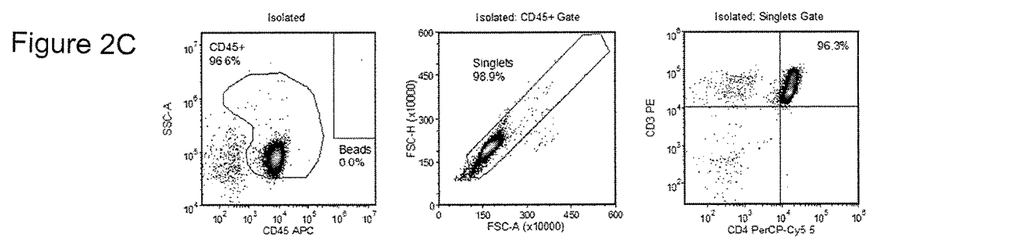

This example demonstrates the enrichment of CD4+ T cells from whole peripheral blood using the method described in Example 7 (FIG. 2). Polyethylene glycol (PEG) functionalized 7 um polystyrene beads were added to the erythrocyte depleted PBMC sample a final ratio of 10 beads to 1 nucleated cell. A CD4+ T cell enrichment cocktail of tetrameric antibody complexes containing antibodies against CD8, CD16, CD19, CD36, CD56, CD66b, TCRγδ and PEG was prepared. A second tetrameric antibody complex containing antibodies against PEG and dextran was prepared. A) FICOLLED™ PBMCs contain 71.5% CD45+ cells with ~47.6% being CD3+ CD4+ T cells. B) The addition of 10 fold excess 7 um PEG polystyrene beads reduces the CD45+ fraction to 7.2% with 83.6% being the beads. The proportion of CD3+ CD4+ T cells in the singlet fraction is similar to the PBMC sample at 44.4%. C) Following the method of the disclosure as outlined in Example 6, the final CD45+ purity is 96.6% and 96.3% of the singlets are CD3+ CD4+ T cells. The recovery of CD3+ CD4+ T cells was 23.6%.

Example 10

Enrichment of Human CD3+ CD4+ T Cells Using MACSxpress with or without Additional Erythrocyte Depletion Using Immunomagnetic Cell Separation.

Figure 5A:
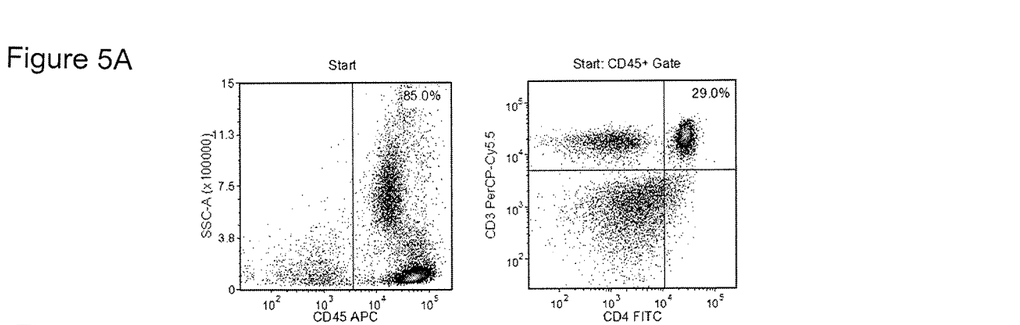
FIGS. 5A-5C show enrichment of human CD3+ CD4+ T cells from human peripheral whole blood using a commercially available erythrocyte aggregation and immunomagnetic separation method MACSxpress with and without the additional immunomagnetic erythrocyte depletion step.
Figure 5B:
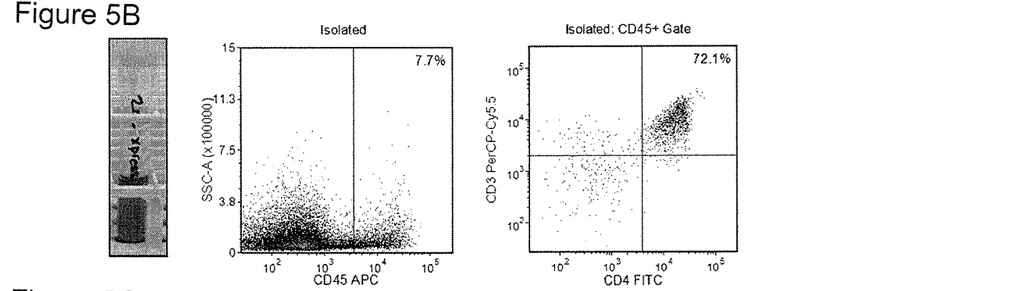
Figure 5C:
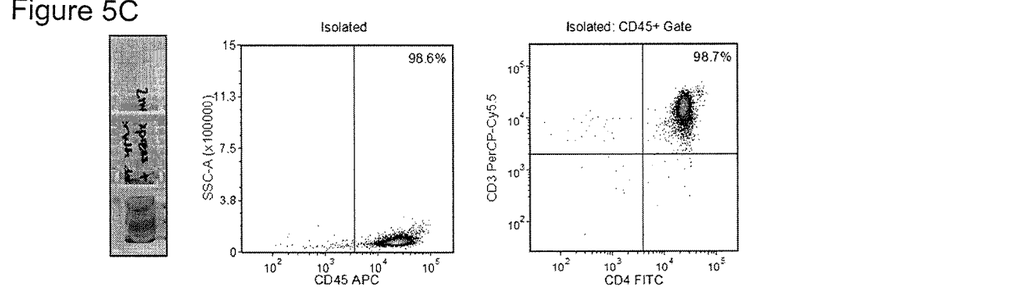

This example demonstrates the negative enrichment of CD3+ CD4+ T cells from 2 mL of human peripheral whole blood using a commercially available erythrocyte aggregation reagent and immunomagnetic separation system (MACSxpress®, Miltenyi Biotech) with and without the additional erythrocyte immunomagnetic depletion step recommended by the manufacturer (FIG. 5). Samples were stained with anti-human CD4 FITC, CD3 PerCP-Cy5.5 and CD45 APC and analyzed by flow cytometry. A) Erythrocytes in human peripheral whole blood were lysed using ammonium chloride resulting in 85.0% CD45+ cells, of which 29.0% were CD3+ CD4+ T cells. A) Following the erythrocyte aggregation and immunomagnetic enrichment protocol as recommended by the manufacturer, the cell suspension is visibly red as shown in the image of the separation tube. Upon analysis of the sample, only 7.7% of recovered cells were CD45+, of which 72.1% were CD3+ CD4+ T cells. B) Following the additional immunomagnetic erythrocyte depletion protocol as per the manufacturers recommendation, the cell suspension is clear of residual erythrocytes. Upon analysis of the sample, 98.6% of the recovered cells were CD45+, of which 98.7% were CD3+ CD4+ T cells. This example demonstrates that the commercially available erythrocyte aggregation reagent and immunomagnetic separation platform MACSxpress requires both an erythrocyte aggregation reagent to sediment erythrocytes combined with a second step involving immunomagnetic erythrocyte depletion step to fully remove erythrocytes from human peripheral whole blood.

Example 11

Enrichment of Human CD3+ T Cells from Human Whole Peripheral Blood Using Either Density Gradient or Immunomagnetic Separation of Immunorosettes, or a Method Combining Erythrocyte Aggregation and Immunomagnetic Separation.

Figure 6:
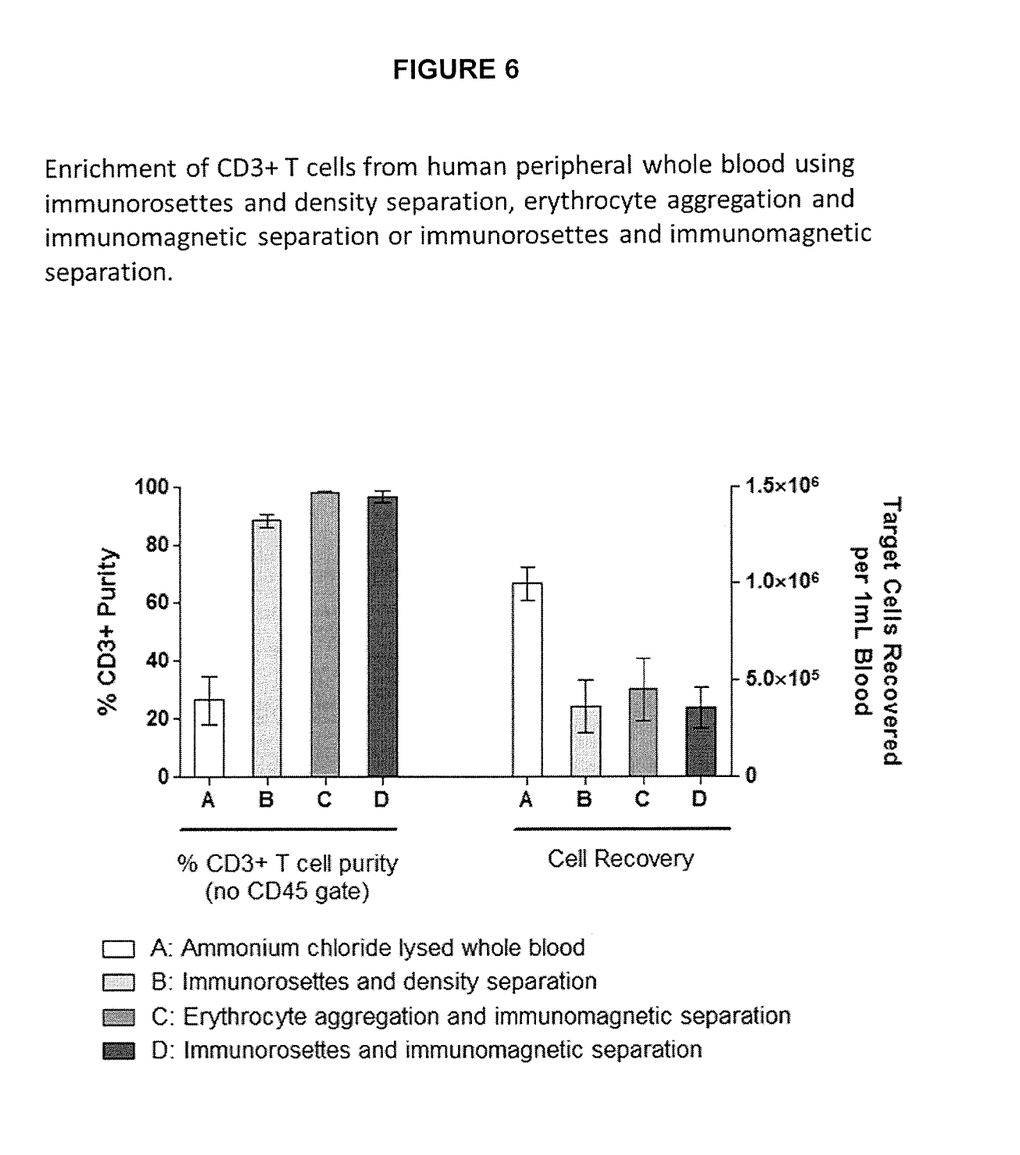
FIG. 6 shows enrichment of human CD3+ T cells from human peripheral whole blood using either A) ammonium chloride lysis, B) immunorosettes and density separation, C) erythrocyte aggregation and immunomagnetic separation, or D) immunorosettes and immunomagnetic separation according to example 3.

This example demonstrates the negative enrichment of CD3+ T cells from 15 mL of human peripheral whole blood (n=3) using either A) ammonium chloride lysis, B) immunorosettes and density separation (RosetteSep, STEMCELL Technologies), C) erythrocyte aggregation and immunomagnetic separation (MACSxpress, Miltenyi Biotech), or D) immunorosettes and immunomagnetic separation according to example 3 (FIG. 6). A) Ammonium chloride lysis of human peripheral blood demonstrates that on average 26.6% of peripheral blood nucleated cells are CD3+ T cells present at $1\times10^6$ cells per mL of whole blood. B) A first antibody composition for the enrichment of CD3+ T cells consisting of a cocktail of tetrameric antibody complexes containing antibodies against CD15, CD16, CD19, CD36, CD56, CD66b, and glycophorin A was prepared. Following immunodensity separation according the U.S. Pat. No. 6,448,075B1, the mean purity of CD3+ T cells within the total cells including residual erythrocytes was 88.7% with $3.6\times10^5$ CD3+ T cells recovered per mL of whole blood. C) Following the negative selection of CD3+ T cells using a commercially available erythrocyte aggregation reagent and immunomagnetic separation product (MACSxpress, Miltenyi Biotech) and an additional erythrocyte depletion step using immunomagnetic cell separation (MACSxpress), the mean purity of CD3+ T cells within the total cells including residual erythrocytes was 98.5% with $4.5\times10^5$ CD3+ T cells recovered per mL of whole blood. D) Following the method of disclosure in example 3, a first antibody composition for the enrichment of CD3+ T cells consisting of a cocktail of tetrameric antibody complexes containing antibodies against CD15, CD16, CD19, CD36, CD56, CD66b, and glycophorin A was prepared. A second antibody composition consisting of a mono-specific tetrameric antibody complex containing antibodies against glycophorin A bound to carboxydextran magnetic particles was prepared. Following the method of the disclosure, mean purities for CD3+ T cells within the total cells including residual erythrocytes was 96.8% with $3.6\times10^5$ CD3+ T cells recovered per mL of whole blood. There was no significant difference between either the purity or CD3+ T cell recovery between methods C) and D). The method of disclosure in example 3, was solely a immunomagnetic negative selection method for the enrichment of CD3+ T cells from whole human peripheral blood.

REFERENCES

1. Ellerman, D. and Scheer, J. M. (2011). Generation of Bispecific Antibodies by Chemical Conjugation. In R. E. Kontermann (Ed.), *Bispecific Antibodies* ($1^{st}$ Edition. pp. 47-63). Heidelberg: Springer Berlin
2. Moldenhauer, G. (2011). Bispecific Antibodies from Hybrid Hybridoma. In R. E. Kontermann (Ed.), *Bispecific Antibodies* ($1^{st}$ Edition. pp. 29-46). Heidelberg: Springer Berlin
3. Chang, C., Rossi, E. A., and Sharkey, R. M. (2011). The Dock-and-Lock (DNL) Approach to Novel Bispecific Antibodies. In R. E. Kontermann (Ed.), *Bispecific Antibodies* ($1^{st}$ Edition. pp. 199-216). Heidelberg: Springer
4. Kim, J. H., and Hong, H. J. (2012). Humanization by CDR Grafting and Specificity-Determining Residue Grafting. In P. Chames (Ed.), *Antibody Engineering: Methods and Protocols* ($2^{nd}$ Edition. pp. 237-245). New York: Humana Press

What is claimed is:
1. A selection method for separating target cells from non-target cells in a sample comprising target cells, secondary targets and non-target cells, the method comprising:
   a) contacting the sample with a first antibody composition comprising both (a) at least one antibody that binds to the target cells and (b) at least one antibody that binds to the secondary targets, wherein the (a) at least one antibody that binds to the target cells is linked, either directly or indirectly, to (b) at least one antibody that binds to the secondary targets, and wherein the contacting is performed under conditions to allow immunorosettes of the target cells and the secondary targets to form;
   b) contacting the sample with particles that are not cells and a second antibody composition comprising

(i) both (a) at least one antibody that binds to the secondary targets either singly or within the immunorosettes, and (b) at least one antibody that binds to a polymer coated on the particles wherein the (a) at least one antibody that binds to the secondary targets is linked, either directly or indirectly, to (b) the at least one antibody that binds to the polymer coated on the particles, or (ii) both (a) at least one antibody that binds to the secondary targets either singly or within the immunorosettes, and (b) at least one antibody that also binds to the secondary targets either singly or within the immunorosettes, wheren the (a) at least one antibody that binds to the secondary targets is linked, either directly or indirectly, to (b) the st least one antibody that binds to the secondary targets to form an antibody complex, the antibody complex directly bound to the particles, or (iii) at least one antibody that binds to the secondary targets either singly or within the immunorosettes, wherein the at least one antibody is directly bound to the particles, under conditions to allow binding of the particles to the immunorosettes and/or the secondary targets to form immunorosette-particle complexes and/or secondary target-particle complexes, and c) separating the immunorosette-particle complexes and/or the secondary target-particle complexes from the sample to separate the target cells from the non-target cells.

2. The method of claim 1 wherein the second antibody composition is bound to the particles prior to contacting with the sample.

3. The method of claim 1 wherein the second antibody composition is bound to the particle and added to the sample prior to contacting the sample with the first antibody composition.

4. The method of claim 1, wherein the secondary targets are erythrocytes, granulocytes, or beads, optionally polystyrene beads.

5. The method of claim 1, wherein the secondary targets are added to the sample.

6. The method of claim 1, wherein the particles are non-magnetic particles.

7. The method of claim 1, wherein the selection method is a positive selection method to select for a desired cell and the target cell are the desired cell or a negative selection method to remove a non-desired cell from the sample and the target cell are the non-desired cell.

8. The method of claim 1, wherein the secondary targets have a density similar to the target cells and the particles have a density different from the target cells.

9. The method of claim 1, wherein the immunorosette-particle complexes are separated from the sample in step c) by density separation or by sedimentation.

10. The method of claim 7, wherein the method further comprises:
    d) separating the target cells from the immunorosettes-particle complexes.

11. The method of claim 8, wherein the target cells are separated from the immunorosette-magnetic particle complexes by physical, chemical, enzymatic or thermal dissociation.

12. The method of claim 4, wherein the method further comprises:
    d) lysis of the erythrocytes in the immunorosettes and
    e) separation of the target cells from the lysed erythrocytes and the particles.

13. The method of claim 1, wherein the sample is blood, whole blood, bone marrow, fetal liver, cord blood, a buffy coat suspension, a leukapheresis sample, a pleural and periotoneal effusion, a sample of thymocytes or a sample of splenocytes.

14. The method of claim 1, wherein the target cells are stem cells, progenitor cells, monocytes, lymphocytes, or granulocytes.

15. The method of claim 14, wherein the lymphocytes are T cells.

* * * * *

UNITED STATES PATENT AND TRADEMARK OFFICE
CERTIFICATE OF CORRECTION

PATENT NO. : 11,325,984 B2
APPLICATION NO. : 16/108707
DATED : May 10, 2022
INVENTOR(S) : Andy Isamu Kokaji It is certified that error appears in the above-identified patent and that said Letters Patent is hereby corrected as shown below:

In the Claims

In Claim 1, at Column 19, Line 13, amend the word "wheren" to "wherein".

In Claim 1, at Column 19, Line 15, amend the word "st" to "at".

In Claim 3, at Column 19, Line 44, amend the word "particle" to "particles".

In Claim 7, at Column 20, Line 7, amend the phrase "target cell" to "target cells".

In Claim 7, at Column 20, Line 9, amend the phrase "target cell" to "target cells".

In Claim 11, at Column 20, Line 21, amend the word "immunorosette-magnetic" to "immunorosette-particle".

In Claim 13, at Column 20, Lines 31 and 32, amend the phrase "a pleural and peritoneal effusion" to "a pleural effusion, a peritoneal effusion".

In Claim 13, at Column 20, Line 32, add a "," after the word "thymocytes".

Signed and Sealed this
Twenty-fifth Day of July, 2023

Katherine Kelly Vidal
*Director of the United States Patent and Trademark Office*